United States Patent
Ouyang et al.

(10) Patent No.: US 9,914,952 B2
(45) Date of Patent: Mar. 13, 2018

(54) STABILIZED LACTATE RESPONSIVE ENZYMES, ELECTRODES AND SENSORS, AND METHODS FOR MAKING AND USING THE SAME

(71) Applicant: Abbott Diabetes Care Inc., Alameda, CA (US)

(72) Inventors: Tianmei Ouyang, Fremont, CA (US); Benjamin J. Feldman, Berkeley, CA (US); Kuan-chou Chen, Alameda, CA (US)

(73) Assignee: Abbott Diabetes Care, Inc., Alameda, CA (US)

( * ) Notice: Subject to any disclaimer, the term of this patent is extended or adjusted under 35 U.S.C. 154(b) by 0 days.

(21) Appl. No.: 15/183,488

(22) Filed: Jun. 15, 2016

(65) Prior Publication Data

US 2016/0362716 A1    Dec. 15, 2016

Related U.S. Application Data

(60) Provisional application No. 62/175,910, filed on Jun. 15, 2015.

(51) Int. Cl.
| | |
|---|---|
| *C12Q 1/00* | (2006.01) |
| *G01N 27/327* | (2006.01) |
| *C12N 9/08* | (2006.01) |
| *C12N 9/96* | (2006.01) |
| *C12N 9/02* | (2006.01) |

(52) U.S. Cl.
CPC ........... *C12Q 1/005* (2013.01); *C12N 9/0065* (2013.01); *C12N 9/0069* (2013.01); *C12N 9/96* (2013.01); *C12Y 111/01006* (2013.01); *C12Y 113/12004* (2013.01)

(58) Field of Classification Search
None
See application file for complete search history.

(56) References Cited

U.S. PATENT DOCUMENTS

| | | | |
|---|---|---|---|
| 5,262,035 A | 11/1993 | Gregg et al. | |
| 5,356,786 A | 10/1994 | Heller et al. | |
| 5,476,776 A * | 12/1995 | Wilkins ............... | A61B 5/1486 204/403.11 |
| 5,593,852 A | 1/1997 | Heller et al. | |
| 5,820,551 A | 10/1998 | Hill et al. | |
| 6,071,391 A | 6/2000 | Gotoh et al. | |
| 6,121,009 A | 9/2000 | Heller et al. | |
| 6,134,461 A | 10/2000 | Say et al. | |
| 6,175,752 B1 | 1/2001 | Say et al. | |
| 6,284,478 B1 | 9/2001 | Heller et al. | |
| 6,377,894 B1 | 4/2002 | Deweese et al. | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,560,471 B1 | 5/2003 | Heller et al. | |
| 6,579,690 B1 | 6/2003 | Bonnecaze et al. | |
| 6,600,997 B2 | 7/2003 | Deweese et al. | |
| 6,605,200 B1 | 8/2003 | Mao et al. | |
| 6,605,201 B1 | 8/2003 | Mao et al. | |
| 6,654,625 B1 | 11/2003 | Say et al. | |
| 6,676,816 B2 | 1/2004 | Mao et al. | |
| 6,736,957 B1 | 5/2004 | Forrow et al. | |
| 6,746,582 B2 | 6/2004 | Heller et al. | |
| 6,881,551 B2 | 4/2005 | Heller et al. | |
| 6,932,894 B2 | 8/2005 | Mao et al. | |
| 7,090,756 B2 | 8/2006 | Mao et al. | |
| 7,299,082 B2 | 11/2007 | Feldman et al. | |
| 7,501,053 B2 | 3/2009 | Karinka et al. | |
| 7,754,093 B2 | 7/2010 | Forrow et al. | |
| 7,811,231 B2 | 10/2010 | Jin et al. | |
| 7,822,557 B2 | 10/2010 | Chen et al. | |
| 8,106,780 B2 | 1/2012 | Goodnow et al. | |
| 8,268,143 B2 | 9/2012 | Liu et al. | |
| 8,435,682 B2 | 5/2013 | Heller | |
| 8,444,834 B2 | 5/2013 | Liu et al. | |
| 2007/0095661 A1 | 5/2007 | Wang et al. | |
| 2010/0198034 A1 | 8/2010 | Thomas et al. | |
| 2010/0213057 A1 | 8/2010 | Feldman et al. | |
| 2010/0324392 A1 | 12/2010 | Yee et al. | |
| 2010/0326842 A1 | 12/2010 | Mazza et al. | |
| 2011/0120865 A1 | 5/2011 | Bommakanti et al. | |
| 2011/0124993 A1 | 5/2011 | Bommakanti et al. | |
| 2011/0124994 A1 | 5/2011 | Bommakanti et al. | |
| 2011/0126188 A1 | 5/2011 | Bernstein et al. | |
| 2011/0213225 A1 | 9/2011 | Bernstein et al. | |
| 2011/0256024 A1 | 10/2011 | Cole et al. | |
| 2011/0257495 A1 | 10/2011 | Hoss et al. | |
| 2012/0138484 A1 * | 6/2012 | Bommakanti ......... | C12Q 1/006 205/777.5 |
| 2012/0150005 A1 | 6/2012 | Hoss et al. | |
| 2012/0157801 A1 | 6/2012 | Hoss et al. | |
| 2012/0245447 A1 | 9/2012 | Karan et al. | |
| 2012/0296186 A1 | 11/2012 | Ouyang et al. | |
| 2012/0323098 A1 | 12/2012 | Moein et al. | |
| 2013/0116524 A1 | 5/2013 | Cole et al. | |
| 2014/0163345 A1 | 6/2014 | Botvinick et al. | |

FOREIGN PATENT DOCUMENTS

| | | | |
|---|---|---|---|
| JP | 2001165892 | * | 12/1999 |
| WO | 2016/065190 | | 4/2016 |

OTHER PUBLICATIONS

Ibupoto et al. Sensors (Basel). 2012;12(3):2456-66.*

(Continued)

*Primary Examiner* — Christian Fronda (74) *Attorney, Agent, or Firm* — Vorys, Sater, Seymour and Pease LLP (57) ABSTRACT

Embodiments of the present disclosure relate to stabilized lactate oxidase compositions, and electrodes, sensors and systems that include the same. Also provided are methods for making the compositions and for detecting and/or measuring lactate in vivo with stable lactate enzyme compositions.

20 Claims, 4 Drawing Sheets

(56) References Cited

OTHER PUBLICATIONS

Schabmueller et al. Biosens Bioelectron. Mar. 15, 2006;21(9):1770-6.*
Cui et al. Biosens Bioelectron. Jun. 15, 2007;22(12):3288-92.*
Motonaka et al et al. Analytica Chimica Acta (1998), 368(1-2), 91-95.*

* cited by examiner

FIG. 4

STABILIZED LACTATE RESPONSIVE ENZYMES, ELECTRODES AND SENSORS, AND METHODS FOR MAKING AND USING THE SAME

CROSS-REFERENCE TO RELATED APPLICATIONS

This application claims priority based on U.S. Provisional Application No. 62/175,910 filed Jun. 15, 2015, the disclosure of which is incorporated by reference herein in its entirety.

INTRODUCTION

Lactate is a key metabolite and its monitoring is of importance for health assessment, including critically ill and/or intensive care and/or surgical patients, for example. However, to date there is no efficient and effective method to monitor lactate, especially over time such as is required for patients in the ICU or surgical suite. Lactate monitoring may be used to detect sepsis, hypoxia, and presence of cancerous tissue (Clinical use of lactate monitoring in critically ill patients Jan Bakker, Maarten W N Nijsten and Tim C Jansen.)

While lactate monitoring is desirable, there are several challenges associated with lactate monitoring such as enzyme stability. Development of improved lactate sensors having a high degree of stability and sensitivity is desirable.

SUMMARY

Embodiments of the present disclosure relate to stabilized lactate enzymes, electrodes, sensors and methods. Disclosed herein are enzyme compositions of lactate responsive enzyme, lactate responsive enzyme stabilizing agent, and polymer. Some or all of these components may be unbound or unconnected, or two or more of these components may be bound or connected together. For example, the enzyme and/or the stabilizer may be bonded to the polymer, e.g., covalently bonded. A mediator may also be included in certain embodiments, and the mediator may be bonded to the polymer, with or without a lactate responsive enzyme and/or a lactate responsive enzyme stabilizing agent being bonded to the polymer. The lactate responsive enzyme may be lactate oxidase and the lactate responsive enzyme stabilizer may be catalase. Also provided are methods for fabricating the stable lactate oxidase enzyme compositions, the lactate electrodes, the lactate sensors, and methods of using the same, for example for lactate monitoring.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "enzymes" encompasses a single enzymes, as well as a combination and/or mixture of two or more different enzymes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular lactates, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The present disclosure discloses lactate enzyme compositions that include lactate responsive enzyme, lactate responsive enzyme stabilizing agent, and polymer that can include sites for attachment of the enzyme and/or stabilizer. A crosslinker and/or an electron transfer agent may also be included. The stabilized lactate enzyme compositions are unchanged (or at least have activity and/or sensitivity and/or specificity that does not change) over periods of time under use conditions of the composition, including use conditions such as temperature, physiological environments, duration, etc., when applied to an electrode and/or an in vivo lactate sensor. A stable and/or unchanged lactate enzyme composition is one that has a less than 10% decrease, including less than 8%, less than 7%, less than 5%, and less than 1%, in signal in a constant concentration of lactate solution over a predetermined time, such as 60 hours, 40 hours, 20 hours, or 10 hours. Changes, if they occur, do not have clinical significance to the lactate monitoring, e.g., do not have statistical significance and/or do not clinically affect the Clark error grid analysis outcome and/or MARD and/or MAD. Changes are at least less than changes to a control composition of a non stabilized lactate responsive enzyme. For example, a change to the lactate stabilized enzyme composition disclosed herein will not result in a change from one zone to another zone of the Clark error grid, or at least will not result in a change to a less accurate zone such as from zone B to zone C, etc. The stabilized lactate responsive enzyme at least remains stabilized up to and throughout the period of time of in vivo use (i.e., the functioning lifetime), e.g., a few weeks to a few months or more-up to a year or more, in an in vivo environment or in an ex-vivo environment that simulates an in vivo environment. In certain embodiments, the lactate responsive enzyme is lactate oxidase and the stabilizer is catalase or its derivatives and mimics (collectively "catalase").

In certain instances, the catalase reduces or eliminates degradation of the lactate oxidase (e.g., denaturation or loss of catalytic activity) by reducing or eliminating degradation of the lactate oxidase caused by oxidative species (e.g., peroxide species, reactive oxygen species, etc.), inhibitors or denaturants. In some embodiments, the catalase reduces the degradation of the lactate oxidase by as much as 2-fold or more, including 5-fold, 8-fold, 10-fold, and as by much as 12-fold as compared to degradation of a lactate oxidase control that will occur in the absence of the catalase. In some embodiments, the catalase reduces the amount of degradation of the lactate oxidase by 20%-80% more as compared to degradation that would occur in the absence of the catalase. The catalase therefore preserves the enzyme's activity over time and over a variety of use conditions.

The lactate oxidase in the enzyme compositions may be present in an amount ranging from 0.05 µg to 5 µg, such as from 0.1 µg to 4 µg, such as from 0.2 µg to 3 µg and including from 0.5 µg to 2 µg. The catalse in the enzyme compositions may be present in an amount ranging from 0.05 µg to 2 µg, such as from 0.1 µg to 1 µg, such as from 0.2 µg to 0.9 µg and including from 0.3 µg to 0.8 µg. In certain embodiments, The weight (w/w) ratio of lactate oxidase to catalase may range from 10 to 1, 8 to 1, 5 to 1, and 2 to 1.

In some embodiments, less than 10% of the enzyme is degraded, in some embodiments less than 5% or even less than 1% or 0.5% or even 0.1%. 5 µg or less of the lactate responsive enzyme is degraded during the time the sensor is in contact with the source of lactate to the time it is out of contact, such as 3 µg or less, such as 2 µg or less and including 1 µg or less of the lactate responsive enzyme. For example, when the catalase stabilizing agent is present in the subject compositions, 5 µg or less of the lactate oxidase is degraded after 3 continuous hours or more, such as 5 continuous hours or more, such as 6 continuous hours or more, such as 12 continuous hours or more, such as 24 continuous hours or more, such as 48 continuous hours or more, such as 72 continuous hours or more and including 168 continuous hours or more.

Unstabilized lactate oxidase may result in a signal decline unrelated to the level of assayed lactate (i.e., because of the enzyme instability) when the enzyme is used to monitor lactate, for example when used with an electrode in an in vivo electrochemical lactate sensor (described in greater detail below). In one example, the catalase stabilizes the activity of the lactate oxidase and provides an in vivo lactate sensor that maintains a stable sensor output (i.e., stable sensor signal such as current or voltage) throughout the duration of the in vivo's sensor wear period and under wear conditions, as noted above. The catalase may stabilize the activity of the lactate oxidase and provide an in vivo lactate sensor that exhibits increased lactate sensitivity and/or specificity as compared to the same lactate sensor without the catalase. In these embodiments, the catalase stabilizes the lactate oxidase such that the stabilized lactate monitoring sensor exhibits a decrease in sensor output of 10% or less of the total sensor output for the duration that the sensor is in contact with the source of lactate, such as by 8% or less, such as by 5% or less, such as 3% or less, such as by 2% or less, such as by 1% or less, such as by 0.1% or less and including by 0.01% or less. In certain embodiments, the catalase stabilizes the lactate oxidase such that the sensor exhibits a decrease in sensor output of 2 nA or less for the duration that the sensor is in contact with the source of lactate, such as by 1.5 nA or less, such as by 1 nA or less, such as by 0.5 nA or less, such as by 0.1 nA or less and including by 0.01 nA or less. In lactate sensors where the stabilizing agent is not present, the sensor exhibits a decrease in signal output that is greater than 10% during the time the lactate sensor is in contact with the source of the lactate. For example, in the absence of the stabilizing agent, lactate sensors may exhibit a decrease in sensor output that is 15% or more, such as by 25% or more, such as by 50% or more and including by 75% or more, which is unrelated to the concentration of lactate.

In some embodiments, the lactate oxidase/catalase compositions increase the lactate sensitivity as compared to sensors without the catalase, e.g., by an increase of 5% or more, such as by 10% or more, such as by 15% or more, such as by 20% or more, such as by 25% or more and including by 50% or more. The lactate oxidase/catalase compositions increase lactate sensor sensitivity of 1 nA/mg/dL or more, such as by 2 nA/mg/dL, such as by 5 nA/mg/dL, such as by 7 nA/mg/dL, such as by 10 nA/mg/dL and including by 15 nA/mg/dL or more. In lactate sensors where the stabilizing agent is not present, the sensor shows no increase in sensitivity and in some cases, exhibits a loss of sensor sensitivity during the lactate sensor is in contact with the source of lactate, such as a decrease in sensor sensitivity of 3% or more, such as by 5% or more, such as by 7% or more and including a decrease in sensor sensitivity of 10% or more. For example, in the absence of stabilizing agent, lactate sensors may exhibit a decrease in sensor sensitivity of 1 nA/mg/dL or more, such as by 2 nA/mg/dL, such as by 5 nA/mg/dL, such as by 7 nA/mg/dL, such as by 10 nA/mg/dL and including by 15 nA/mg/dL or more during the time when the sensor is in contact with the source of lactate.

The lactate oxidase/catalase compositions may be heterogeneous or homogenous. In some embodiments, both are distributed throughout the composition, e.g., when applied to an electrode. For example, lactate oxidase and catalase may be distributed uniformly throughout the composition, such that the concentration of each of the lactate oxidase and catalase are the same throughout. In some cases, the compositions have a homogeneous distribution of the lactate oxidase and catalase. In certain instances, the lactate oxidase/catalase composition further includes an electron transfer agent that is also distributed throughout the composition. In certain embodiments, all three of the lactate responsive enzyme, stabilizing agent and electron transfer agent are distributed uniformly throughout the composition.

The stabilized in vivo lactate sensors discussed detect and/or monitor lactate in biological fluid in vivo. In some embodiments, these in vivo lactate sensors may detect and/or monitor lactate in one or more of interstitial fluid, blood and its constituents, dermal fluid, mucus, lymphatic fluid, synovial fluid, cerebrospinal fluid, saliva, bronchoalveolar lavage, amniotic fluid, and amniotic cord blood.

In some embodiments, the subject is a human. The sensors described herein may be applied to samples from subjects of any gender and at any stage of development (i.e., fetal, neonates, infant, juvenile, adolescent and adult), while in certain embodiments the subject is a juvenile, adolescent or adult. While the present disclosure is described in the context of human subjects, it is to be understood that the sensors may also be configured to analyze samples from other animal subjects (that is, in "non-human" subjects"), such as but not limited to, dogs, cats, birds, mice, rates, guinea pigs, chimpanzees, monkeys and other primates, livestock and horses. In some embodiments, lactate sensors of interest are in vivo sensors configured such that at least a portion of the sensor is positioned in the subject. For example, all or a part of the lactate oxidase stabilized sensor may be positioned beneath the skin surface of the user to contact bodily fluid directly to detect and/or monitor lactate over a period of time.

The lactate oxidase/catalase compositions may include an electron transfer agent. They may be electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736, 957, 7,501,053 and 7,754,093, the disclosures of each of which are incorporated herein by reference in their entirety. Although any organic, organometallic or inorganic redox species may be bound to the polymer and used as an electron transfer agent, in certain embodiments the electron transfer agent is a transition metal compound or complex, e.g., osmium, ruthenium, iron, and cobalt compounds or complexes.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to the polymer and used as an electron transfer agent, in certain embodiments the electron transfer agent is a transition metal compound or complex, e.g., osmium, ruthenium, iron, and cobalt compounds or complexes. Examples of electron transfer agents and polymer-bound electron transfer agents of interest include, but are not limited to, the transition metal complexes described in U.S. Pat. Nos. 8,444,834, 8,268,143 and 6,605,201, the disclosures of which are herein incorporated by reference in their entirety.

The lactate oxidase/catalase compositions described herein are polymeric. Polymers that may be used may be branched or unbranched and may be homopolymers formed from the polymerization of a single type of monomer or heteropolymers that include two or more different types of monomers. Heteropolymers may be copolymers where the copolymer has alternating monomer subunits, or in some cases, may be block copolymers, which include two or more homopolymer subunits linked by covalent bonds (e.g, diblock or triblock copolymers).

In some embodiments, the subject lactate oxidase/catalase compositions include a heterocycle-containing polymer. The term heterocycle (also referred to as "heterocycicyl") is used herein in its conventional sense to refer to any cyclic moiety which includes one or more heteroatoms (i.e., atoms other than carbon) and may include, but are not limited to N, P, O, S, Si, etc. Heterocycle-containing polymers may be heteroalkyl, heteroalkanyl, heteroalkenyl and heteroalkynyl as well as heteroaryl or heteroarylalkyl.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

In some embodiments, the heterocycle-containing component is an aromatic ring system. "Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

In certain embodiments, the lactate oxidase/catalase compositions include a heterocyclic nitrogen containing component, such as polymers of polyvinylpyridine (PVP) and polyvinylimidazole.

The polymeric lactate oxidase/catalase compositions may also include one or more crosslinkers (crosslinking agent) such that the polymeric backbone enzyme composition is crosslinked. As described herein, reference to linking two or more different polymers together is intermolecular crosslinking, whereas linking two more portions of the same polymer is intramolecular crosslinking. In embodiments of the present disclosure, crosslinkers may be capable of both intermolecular and intramolecular crosslinkings at the same time.

Suitable crosslinkers may be bifunctional, trifunctional or tetrafunctional, each having straight chain or branched structures. Crosslinkers having branched structures include a multi-arm branching component, such as a 3-arm branching component, a 4-arm branching component, a 5-arm branching component, a 6-arm branching component or a larger number arm branching component, such as having 7 arms or more, such as 8 arms or more, such as 9 arms or more, such as 10 arms or more and including 15 arms or more. In certain instances, the multi-arm branching component is a multi-arm epoxide, such as 3-arm epoxide or a 4-arm epoxide. Where the multi-arm branching component is a multi-arm epoxide, the multi-arm branching component may be a polyethylene glycol (PEG) multi-arm epoxide or a non-polyethylene glycol (non-PEG) multi-arm epoxide. In some embodiments, the multi-arm branching component is a non-PEG multi-arm epoxide. In other embodiments, the multi-arm branching component is a PEG multi-arm epoxide. In certain embodiments, the multi-arm branching component is a 3-arm PEG epoxide or a 4-arm PEG epoxide.

Examples of crosslinkers include but are not limited to polyethylene glycol diglycidyl ether, N,N-diglycidyl-4-glycidyloxyaniline as well as nitrogen-containing multi-functional crosslinkers having the structures:

In some instances, one or more bonds with the one or more of the lactate responsive enzyme, the stabilizing agent and the electron transfer agent may be formed. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the lactate oxidase/catalase compositions can form crosslinks between the polymers of the composition and the lactate responsive enzyme, the stabilizing agent and the electron transfer agent. In certain embodiments, crosslinking of the polymer to the one or more of the lactate responsive enzyme, the stabilizing agent and the electron transfer agent facilitates a reduction in the occurrence of delamination of the enzyme compositions from an electrode.

As described herein, the stabilized lactate oxidase/catalase compositions may be used with a lactate sensor. A lactate sensor may have one or more electrodes with the stabilized lactate-responsive enzyme composition. In embodiments, the lactate sensor includes: a working electrode having a conductive material the subject enzyme composition proximate to (e.g., disposed on) and in contact with the conductive material. One or more other electrode may be included such as one or more counter electrodes, one or more reference electrodes and/or one or more counter/reference electrodes.

The particular configuration of electrochemical sensors may depend on the use for which the lactate sensor is intended and the conditions under which the lactate sensor will operate. In certain embodiments of the present disclosure, lactate sensors are in vivo wholly positioned lactate sensors or transcutaneously positioned lactate sensors configured for in vivo positioning in a subject. In one example, at least a portion of the lactate sensor may be positioned in the subcutaneous tissue for testing lactate concentrations in interstitial fluid. In another example, at least a portion of the lactate sensor may be positioned in the dermal tissue for testing lactate concentration in dermal fluid.

In embodiments, one or more of the subject enzyme compositions is positioned proximate to (e.g., disposed on) the surface of a working electrode. In some instances, a plurality of enzyme compositions are positioned proximate to the surface of working electrode (e.g., in the form of spots). In certain cases, a discontinuous or continuous perimeter is formed around each of the plurality of enzyme compositions positioned proximate to the surface of the working electrode. Examples of depositing a plurality of reagent compositions to the surface of an electrode as well as forming a discontinuous or continuous perimeter around each reagent composition is described in U.S. Patent Publication No. 2012/0150005 and in U.S. Patent Application No. 62/067,813, the disclosures of which are herein incorporated by reference.

The stabilized lactate oxidase/catalase composition may be deposited onto the surface of the working electrode as one large application which covers the desired portion of the working electrode or in the form of an array of a plurality of stabilized lactate oxidase/catalase compositions, e.g., spaced apart from each other. Depending upon use, any or all of the enzyme compositions in the array may be the same or different from one another. For example, an array may include two or more, 5 or more, 10 or more, 25 or more, 50 or more, 100 or more stabilized lactate oxidase/catalase composition array features, or even 1000 or more, in an area of 100 $mm^2$ or less, such as 75 $mm^2$ or less, or 50 $mm^2$ or less, for instance 25 $mm^2$ or less, or 10 $mm^2$ or less, or 5 $mm^2$ or less, such as 2 $mm^2$ or less, or 1 $mm^2$ or less, 0.5 $mm^2$ or less, or 0.1 $mm^2$ or less.

The shape of deposited stabilized lactate oxidase/catalase composition may vary within or between sensors. For example, in certain embodiments, the deposited membrane is circular. In other embodiments, the shape will be of a triangle, square, rectangle, circle, ellipse, or other regular or irregular polygonal shape (e.g., when viewed from above) as well as other two-dimensional shapes such as a circle, half circle or crescent shape. All or a portion of the electrode may be covered by the stabilized lactate oxidase/catalase composition, such as 5% or more, such as 25% or more, such as 50% or more, such as 75% or more and including 90% or more. In certain instances, the entire electrode surface is covered by the enzyme composition (i.e., 100%).

Fabricating an electrode and/or sensor according to embodiments of the present disclosure produces a reproducible stabilized lactate oxidase/catalase composition deposited on the surface of the electrode. For example, enzyme compositions provided herein may deviate from each other by 5% or less, such as by 4% or less, such as by 3% or less, such as by 2% or less, such as by 1% or less and including by 0.5% or less. In certain embodiments, deposited stabilized lactate oxidase/catalase composition shows no deviation from one another and are identical.

In certain embodiments, methods further include drying stabilized lactate oxidase/catalase composition deposited on the electrode. Drying may be performed at room temperature, at an elevated temperature, as desired, such as at a temperature ranging from 25° C. to 100° C., such as from 30° C. to 80° C. and including from 40° C. to 60° C.

Examples of configurations for the subject lactate sensors and methods for fabricating them may include, but are not limited to, those described in U.S. Pat. Nos. 6,175,752, 6,134,461, 6,579,690, 6,605,200, 6,605,201, 6,654,625, 6,746,582, 6,932,894, 7,090,756, 5,356,786, 6,560,471, 5,262,035, 6,881,551, 6,121,009, 6,071,391, 6,377,894, 6,600,997, 6,514,460, 5,820,551, 6,736,957, 6,503,381, 6,676,816, 6,514,718, 5,593,852, 6,284,478, 7,299,082, 7,811,231, 7,822,557 8,106,780, and 8,435,682; U.S. Patent Application Publication Nos. 2010/0198034, 2010/0324392, 2010/0326842, 2007/0095661, 2010/0213057, 2011/0120865, 2011/0124994, 2011/0124993, 2010/0213057, 2011/0213225, 2011/0126188, 2011/0256024, 2011/0257495, 2012/0157801, 2012/0245447, 2012/0157801, 2012/0323098, and 20130116524, the disclosures of each of which are incorporated herein by reference in their entirety.

In some embodiments, in vivo sensors may include an insertion tip positionable below the surface of the skin, e.g., penetrating through the skin and into, e.g., the subcutaneous space, in contact with the user's biological fluid such as interstitial fluid. Contact portions of working electrode, a reference electrode and a counter electrode are positioned on the first portion of the sensor situated above the skin surface. A working electrode, a reference electrode and a counter electrode are positioned at the inserted portion of the sensor. Traces may be provided from the electrodes at the tip to a contact configured for connection with sensor electronics.

In certain embodiments, the working electrode and counter electrode of the sensor as well as dielectric material of are layered. For example, the sensor may include a non-conductive material layer, and a first conductive layer such as conductive polymer, carbon, platinum-carbon, gold, etc., disposed on at least a portion of the non-conductive material layer (as described above). The stabilized lactate oxidase/catalase composition is positioned on one or more surfaces of the working electrode, or may otherwise be directly or indirectly contacted to the working electrode. A first insulation layer, such as a first dielectric layer may disposed or layered on at least a portion of a first conductive layer and a second conductive layer may be positioned or stacked on top of at least a portion of a first insulation layer (or dielectric layer). The second conductive layer may be a reference electrode. A second insulation layer, such as a second dielectric layer may be positioned or layered on at least a portion of the second conductive layer. Further, a third conductive layer may be positioned on at least a portion of the second insulation layer and may be a counter electrode. Finally, a third insulation layer may be disposed or layered on at least a portion of the third conductive layer. In this manner, the sensor may be layered such that at least a portion of each of the conductive layers is separated by a respective insulation layer (for example, a dielectric layer).

In other embodiments, some or all of the electrodes may be provided in a co-planar manner such that two or more electrodes may be positioned on the same plane (e.g., side-by side (e.g., parallel) or angled relative to each other) on the material. For example, co-planar electrodes may include a suitable spacing there between and/or include a dielectric material or insulation material disposed between the conductive layers/electrodes. Furthermore, in certain embodiments one or more of the electrodes may be disposed on opposing sides of the non-conductive material. In such embodiments, electrical contact may be on the same or different sides of the non-conductive material. For example, an electrode may be on a first side and its respective contact may be on a second side, e.g., a trace connecting the electrode and the contact may traverse through the material. A via provides an avenue through which an electrical trace is brought to an opposing side of a sensor.

The subject in vivo lactate sensors be configured for monitoring the level of the lactate over a time period which may range from seconds, minutes, hours, days, weeks, to months, or longer. Suitable temperature independent membranes may include, but are not limited to those described in U.S. Patent Publication No. 2012/0296186 and U.S. Patent Application No. 62/067,813, the disclosure of which are herein incorporated by reference.

In vivo lactate sensors according to certain embodiments may be configured to operate at low oxygen concentration. By low oxygen concentration is meant the concentration of oxygen is 1.5 mg/L or less, such as 1.0 mg/L or less, such as 0.75 mg/L or less, such as 0.6 mg/L or less, such as 0.3 mg/L or less, such as 0.25 mg/L or less, such as 0.15 mg/L or less, such as 0.1 mg/L or less and including 0.05 mg/L or less.

Aspects of the present disclosure also include methods for in vivo monitoring lactate levels over time with stabilized lactate oxidase. Generally, monitoring the concentration of lactate in a fluid of the body of a subject includes inserting at least partially under a skin surface a lactate oxidase/catalase in vivo lactate sensor as disclosed herein, contacting the monitored fluid (interstitial, blood, dermal, and the like) with the inserted lactate oxidase/catalase sensor, and generating a sensor signal at the working electrode. The presence and/or concentration of lactate detected by the lactate sensor may be displayed, stored, forwarded, and/or otherwise processed.

A variety of approaches may be employed to determine the concentration of lactate with the subject sensors. In certain aspects, an electrochemical lactate concentration monitoring approach is used. For example, monitoring the concentration of lactate using the sensor signal may be performed by coulometric, amperometric, voltammetric, potentiometric, or any other convenient electrochemical detection technique.

These methods may also be used in connection with a device that is used to detect and/or measure another analyte, including glucose, oxygen, carbon dioxide, electrolytes, or other moieties of interest, for example, or any combination thereof, found in a bodily fluid, including subcutaneous e.g., interstitial fluid, dermal fluid, blood or other bodily fluid of interest or any combination thereof.

In certain embodiments, the method further includes attaching an electronics unit to the skin of the patient, coupling conductive contacts of the electronics unit to contacts of the lactate sensor, collecting data using the electronics unit regarding a level of lactate from signals generated by the sensor, and forwarding the collected data from electronics unit to a receiver unit, e.g., by RF. The receiver unit may be a mobile telephone. The mobile telephone may include a lactate application. In certain embodiments, lactate information is forwarded by RFID protocol, Bluetooth, and the like.

The lactate sensor may be positionable in a user for automatic lactate sensing, either continuously or periodically. Embodiments may include monitoring the level of the lactate over a time period which may range from seconds, minutes, hours, days, weeks, to months, or longer. Future lactate levels may be predicted based on information obtained, e.g., the current lactate level at time zero as well as a lactate rate of change.

The sensor electronics unit may automatically forward data from the lactate sensor/electronics unit to one or more receiver units. The sensor data may be communicated automatically and periodically, such as at a certain frequency as data is obtained or after a certain time period of sensor data stored in memory. For example, sensor electronics coupled to an in vivo positioned sensor may collect the sensor data for a predetermined period of time and transmit the collected data periodically (e.g., every minute, five minutes, or other predetermined period) to a monitoring device that is positioned in range from the sensor electronics.

In other embodiments, the sensor electronics coupled to the in vivo positioned sensor may communicate with the receiving device non automatically manner and not set to any specific schedule. For example, the sensor data may be communicated from the sensor electronics to the receiving device using RFID technology, and communicated whenever the sensor electronics are brought into communication range of the lactate monitoring device. For example, the in vivo positioned sensor may collect sensor data in memory until the monitoring device (e.g., receiver unit) is brought into communication range of the sensor electronics unit—e.g., by the patient or user. When the in vivo positioned sensor is detected by the monitoring device, the device establishes communication with the lactate sensor electronics and uploads the sensor data that has been collected since the last transfer of sensor data, for instance. In this way, the patient does not have to maintain close proximity to the receiving device at all times, and instead, can upload sensor data when desired by bringing the receiving device into range of the lactate sensor. In yet other embodiments, a combination of automatic and non-automatic transfers of sensor data may be implemented in certain embodiments. For example, transfers of sensor data may be initiated when brought into communication range, and then continued on an automatic basis if continued to remain in communication range.

Aspects of the present disclosure include methods for fabricating an electrode having a stabilized lactate oxidase/catalase composition for use in a lactate sensor. Embodiments include forming an electrode and positioning the stabilized lactate oxidase/catalase composition proximate the electrode. Some embodiments include applying a conductive layer to the surface of a non-conductive material, removing a portion of the conductive layer to define an electrode on the surface of the material, removing at least a portion in the conductive layer within the boundary of the electrode to form an area on the electrode having an incomplete perimeter and depositing the stabilized lactate oxidase/catalase composition within the boundaries of the enzyme composition of the electrode.

EXPERIMENTAL

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Experiments were performed to demonstrate the performance of lactate oxidase sensors in the presence and absence of catalase. Lactate sensors were prepared by depositing onto the surface of an electrode a reagent composition having lactate oxidase, and a polymer bound osmium-transition metal catalyst and a difunctional crosslinker, as shown by the scheme below:

The lactate sensors were tested in phosphate buffer containing 5 mM lactate at 33° C.

under 1% oxygen. The temperature was controlled by a water circulated system with a digital temperature controller.

Figure 1:
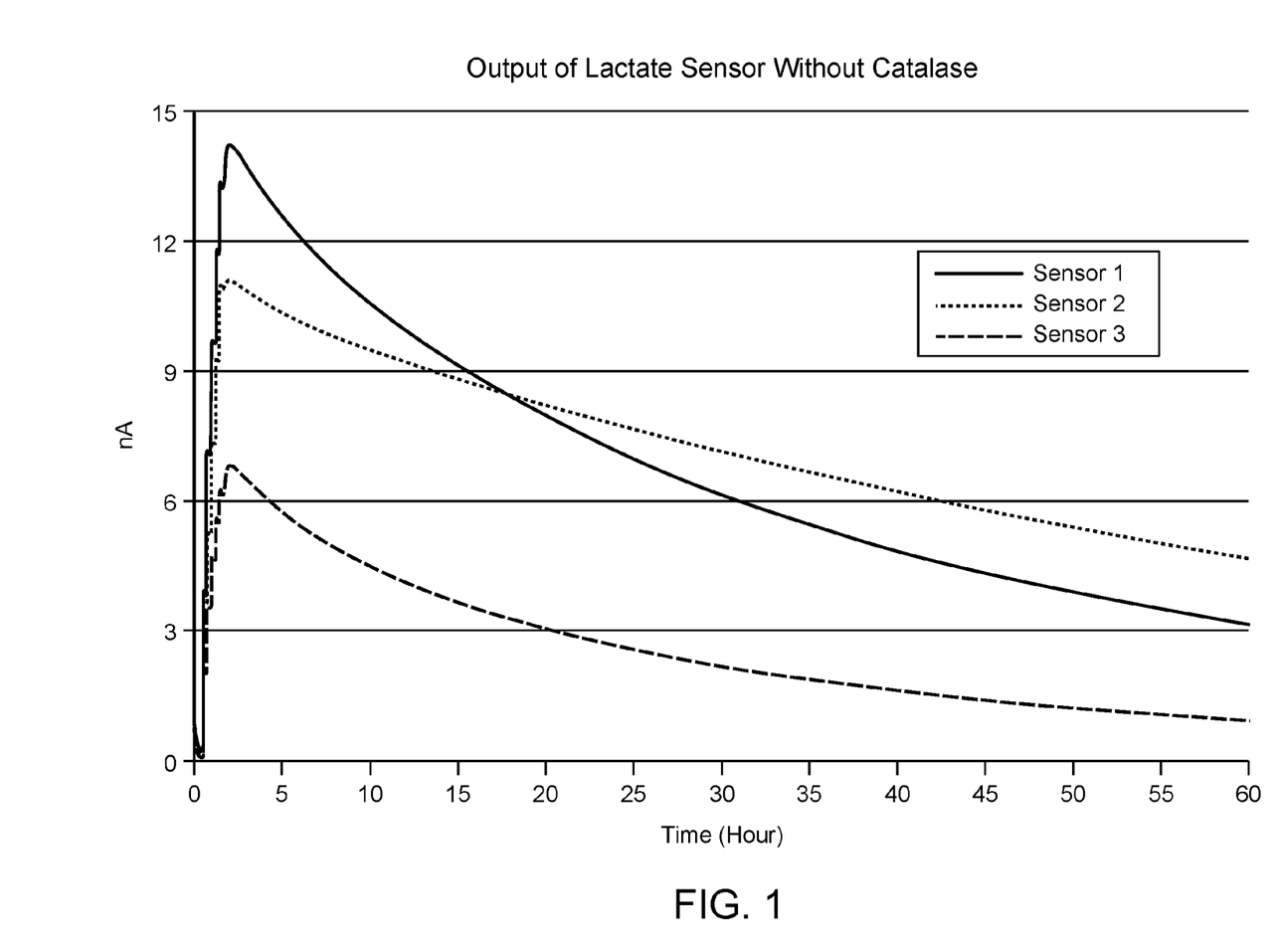
FIG. 1 shows a graph of sensor signal output as a function of time for three lactate sensors that do not include a stabilizing agent as a part of the sensor enzyme composition.

FIG. 1 shows the stability of sensor signal output over the course of 60 continuous hours for three different lactate sensors that include enzyme compositions having lactate oxidase, a polymer bound transition metal complex and a crosslinker. As shown in FIG. 1, the lactate sensors began to exhibit a drop in sensor output after 3 hours of use and showed a significant and continuous decrease in signal output until 60 hours was reached, i.e., they are unstable. The lactate sensors exhibited a decrease of greater than 70% of the signal output over the course of the 60 hours the lactate sensors were in contact with lactate.

Example 2

Experiments were performed to compare the performance of lactate sensors with and without catalase with the lactate oxidase composition. Sensors lacking stabilizing agent were prepared as described above in Example 1. Sensors with enzyme compositions which include catalase were prepared by depositing onto the surface of an electrode a reagent composition having lactate oxidase, the stabilizing agent catalase, and a polymer bound osmium-transition metal catalyst and a difunctional crosslinker, as shown by the scheme below:

Each lactate sensor was tested in phosphate buffer containing lactate at 33° C. under 1% oxygen. The temperature was controlled by a water circulated system with a digital temperature controller.

Figure 2:
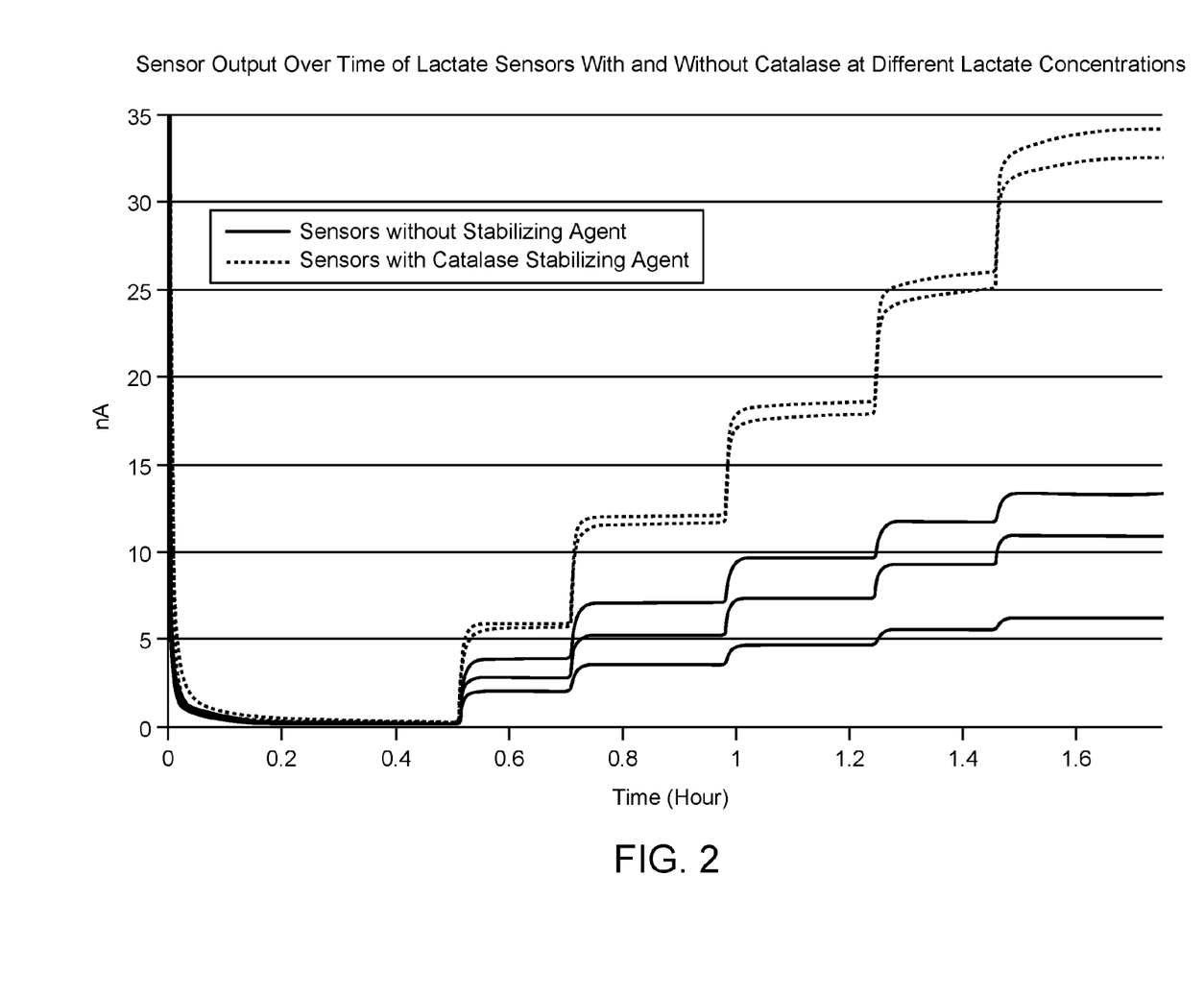
FIG. 2 shows a graph of sensor signal output over time in response to stepwise changes in lactate concentration for lactate sensors lacking a stabilizing agent and lactate sensors having a stabilizing agent as a part of the enzyme composition.

FIG. 2 shows the signal output from each sensor during calibration studies which illustrates sensor response to stepwise changes in the concentration of lactate from 1 mM to 5 mM. Lactate sensors lacking catalase exhibited a smaller signal response to each increase in lactate concentration and a lower overall signal output over time than the catalase-containing sensors. Lactate sensors having catalase as a part of the enzyme composition exhibited large changes in signal response at each increase in lactate concentration and a higher overall signal output over time as compared to lactate sensors in absence of catalase.

Figure 3:
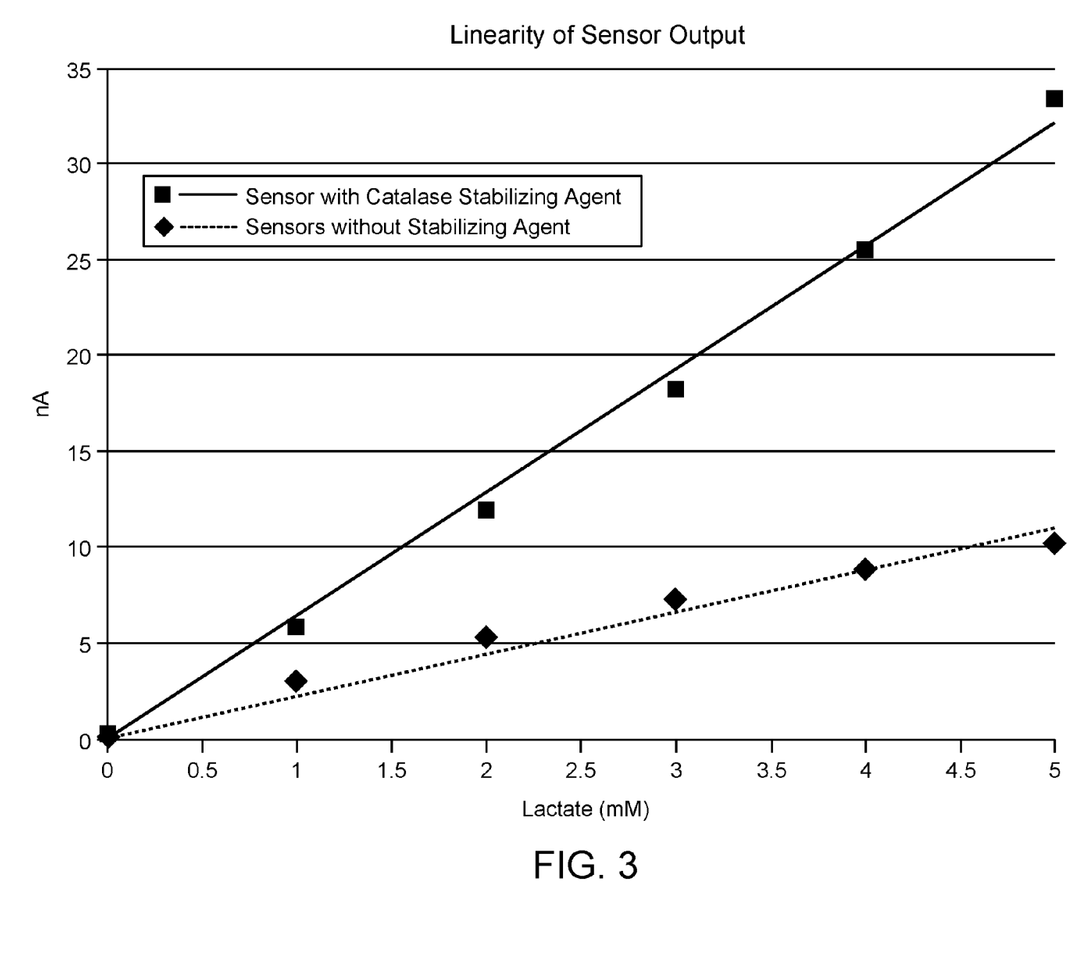
FIG. 3 shows a graph of sensor signal output as a function of lactate concentration for lactate sensors lacking a stabilizing agent and lactate sensors having a stabilizing agent as a part of the enzyme composition.

FIG. 3 shows the linearity of sensor signal output as a function of lactate concentration. Lactate sensors lacking catalase exhibited a lower slope, demonstrating a lower sensitivity of these lactate sensors than that of the sensors that included the lactate oxidase/catalase compositions. Lactate sensors having catalase a part of the enzyme composition exhibited a slope nearly three times greater than the lactate sensors lacking catalase.

Figure 4:
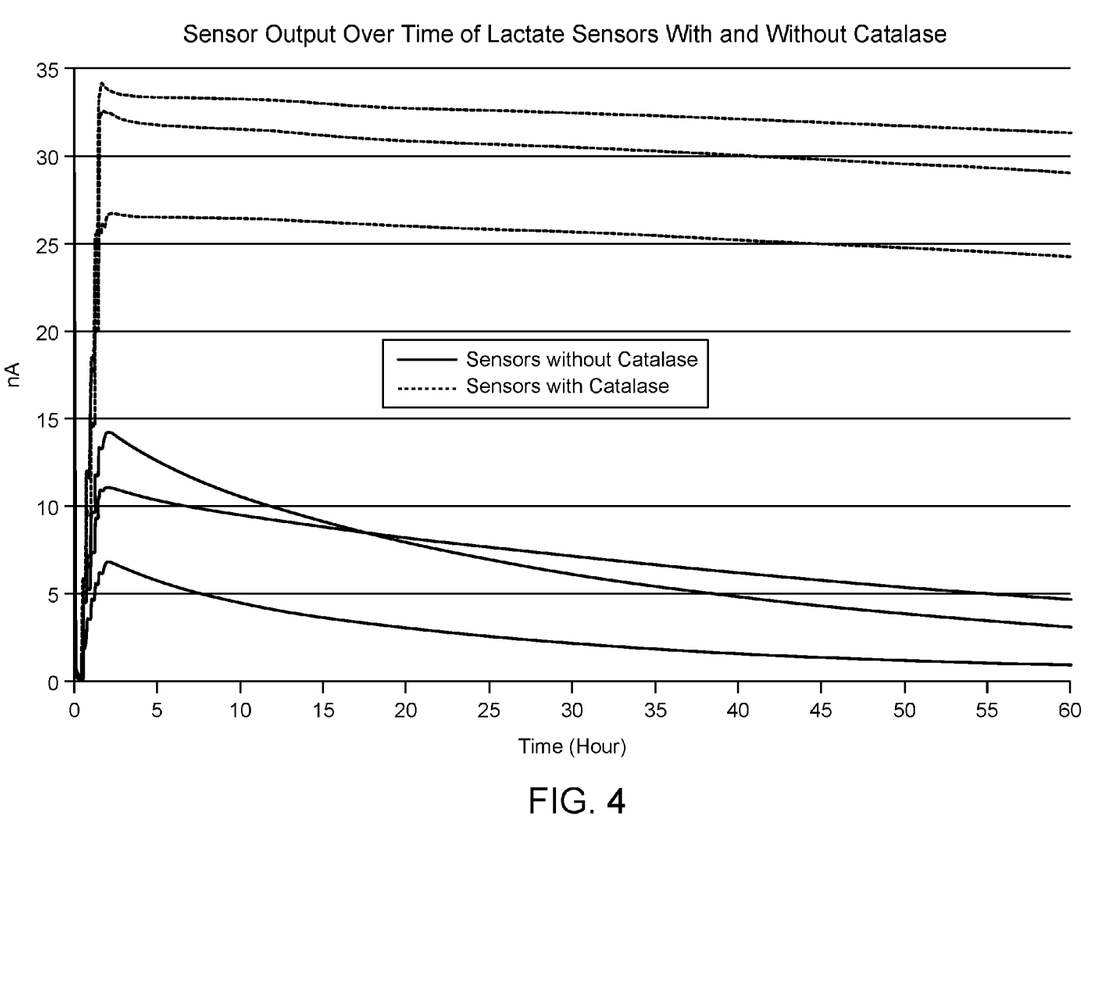
FIG. 4 shows a graph of sensor signal output stability as a function of time for lactate sensors lacking a stabilizing agent and lactate sensors having a stabilizing agent as a part of the enzyme composition.

FIG. 4 shows the stability of sensor signal output over the course of 60 continuous hours for three lactate sensors that lacked catalase and three lactate sensors having catalase as a part of the enzyme composition. As shown in FIG. 4, the lactate sensors that lacked catalase begin to exhibit a drop in sensor output after 3 hours of use and showed a significant and continuous decrease in signal output until 60 hours was reached. The lactate sensors that lacked catalase exhibited a decrease of greater than 70% of the signal output over the course of the 60 hours the lactate sensors were in contact with lactate. In contrast, lactate sensors having catalase as a part of the lactate oxidase enzyme composition exhibited significantly lower decrease in signal output (8%) over the 60 hour testing.

A summary of the comparison between lactate sensors that lacked catalase and lactate sensors having catalase as a part of the enzyme composition is provided in Table 1.

TABLE 1

| | Sensor without Catalase | Sensors with Catalase |
|---|---|---|
| Slope | 2.2 | 6.4 |
| $R^2$ | 0.9651 | 0.9947 |
| Signal Decrease after 60 hours | −71% | −8% |

That which is claimed is:

1. A lactate sensor comprising an enzyme composition that comprises:
   a lactate responsive enzyme; and
   a stabilizing agent that stabilizes the lactate responsive enzyme in a manner sufficient to provide a sensor signal that changes by 10% or less for 60 continuous hours or more,
      wherein the lactate responsive enzyme is lactate oxidase and the stabilizing agent is catalase, present in the enzyme composition in a weight (w/w) ratio of lactate oxidase to catalase ranging from 10 to 1 to 2 to 1.

2. The lactate sensor according to claim 1, wherein the enzyme composition comprises a heterocycle-containing polymer and a crosslinker.

3. The lactate sensor according to claim 2, wherein the lactate responsive enzyme and stabilizing agent are crosslinked within the polymer.

4. The lactate sensor according to claim 2, wherein the lactate responsive enzyme and stabilizing agent are covalently bonded to the polymer.

5. The lactate sensor according to claim 1, wherein the stabilizing agent stabilizes the lactate responsive enzyme in a manner sufficient to provide a sensor signal that changes by 10% or less for 168 continuous hours or more.

6. The lactate sensor according to claim 5, wherein the stabilizing agent stabilizes the lactate responsive enzyme in a manner sufficient to provide a sensor signal that changes by 5% or less for 168 continuous hours or more.

7. The lactate sensor according to claim 1, wherein the stabilizing agent increases sensor sensitivity to lactate as compared to a lactate sensor that does not include the stabilizing agent.

8. The lactate sensor according to claim 7, wherein the stabilizing agent increases sensor sensitivity to lactate for 60 continuous hours or more.

9. The lactate sensor according to claim 8, wherein the stabilizing agent increases sensor sensitivity by 10% or more as compared to a lactate sensor that does not include the stabilizing agent.

10. The lactate sensor according to claim 1, wherein the enzyme composition further comprises an electron transfer agent.

11. The lactate sensor according to claim 10, wherein the electron transfer agent is an osmium-containing complex.

12. The lactate sensor according to claim 10, wherein the electron transfer agent is covalently bonded to the polymer.

13. The lactate sensor according to claim 1, wherein the lactate sensor comprises a working electrode and a counter electrode.

14. The lactate sensor according to claim 13, wherein the enzyme composition is positioned proximate to a working electrode.

15. The lactate sensor according to claim 14, wherein the enzyme composition is fixed to the working electrode.

16. The lactate sensor according to claim 1, wherein the lactate oxidase is present in the enzyme composition in an amount ranging from 0.05 µg to 5 µg.

17. The lactate sensor according to claim 1, wherein the catalase is present in the enzyme composition in an amount ranging from 0.05 µg to 2 µg.

18. The lactate sensor according to claim 1, wherein the stabilizing agent stabilizes the lactate responsive enzyme in a manner such that the lactate sensor exhibits a decrease in sensor output of 2 nA or less during exposure to lactate as compared to a lactate sensor that does not include the stabilizing agent.

19. The lactate sensor according to claim 1, wherein the stabilizing agent increases sensor sensitivity to lactate in an amount ranging from 1 nA/mg/dL to 15 nA/mg/dL or more as compared to a lactate sensor that does not include the stabilizing agent.

20. A lactate sensor comprising an enzyme composition that comprises:
   a polymer;
   a lactate responsive enzyme; and
   a stabilizing agent,
      wherein the lactate responsive enzyme is lactate oxidase and the stabilizing agent is catalase, present in the enzyme composition in a weight (w/w) ratio of lactate oxidase to catalase ranging from 10 to 1 to 2 to 1, and
   wherein the catalase is covalently bonded to the polymer.

* * * * *